United States Patent
Nellenbach et al.

(10) Patent No.: US 11,219,558 B2
(45) Date of Patent: Jan. 11, 2022

(54) METHOD FOR MOVING ARTICLES AND CONTROLLING THE POSITION OF SAME

(71) Applicant: The Procter & Gamble Company, Cincinnati, OH (US)

(72) Inventors: Eva Grace Nellenbach, Reading, OH (US); Hinrich Knuth, Mason, OH (US); Matthew Howard Wasson, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 432 days.

(21) Appl. No.: 15/894,976

(22) Filed: Feb. 13, 2018

(65) Prior Publication Data
US 2018/0161214 A1 Jun. 14, 2018

Related U.S. Application Data

(63) Continuation of application No. 13/910,551, filed on Jun. 5, 2013, now abandoned, which is a
(Continued)

(51) Int. Cl.
*A61F 13/26* (2006.01)
*B29C 69/02* (2006.01)
(Continued)

(52) U.S. Cl.
CPC ............ *A61F 13/266* (2013.01); *A61F 6/005* (2013.01); *A61F 13/15764* (2013.01);
(Continued)

(58) Field of Classification Search
CPC .............. A61F 13/2097; A61F 13/2082; A61F 13/266; A61F 13/20; A61F 13/2077; B29C 205/0827; B29C 67/0007
(Continued)

(56) References Cited

U.S. PATENT DOCUMENTS

| 2,935,175 A | 5/1960 | Wurgaft |
| 2,965,175 A | 12/1960 | Wurgaft |

(Continued)

FOREIGN PATENT DOCUMENTS

| DE | 1431650 A1 | 1/1969 |
| DE | 2125551 B1 | 7/1972 |

(Continued)

OTHER PUBLICATIONS

"Annealing", Merriam-Webster Dictionary. <http://www.merriam-webster.com/dictionary/anneal>. Jun. 23, 2007.
(Continued)

*Primary Examiner* — Tatyana Zalukaeva
*Assistant Examiner* — Meagan Ngo
(74) *Attorney, Agent, or Firm* — William E. Gallagher; Andrew J. Hagerty

(57) ABSTRACT

A method for altering the appearance of molded articles is described herein. The method includes the steps of providing a plurality of articles; feeding a first article to a conveyor; transporting the first article to a treatment station; activating an activatable colorant of the first article by exposing the first article to at least one energy source, thereby causing a color change in the first article; manipulating the exposure of the first article to create a first discernable pattern in the first article; feeding a second article to the conveyor; transporting the second article to the treatment station; activating an activatable colorant of the second article by exposing the second article to the at least one energy source, thereby causing a color change in the second article; and manipulating the exposure of the second article to create a second discernable pattern in the second article.

8 Claims, 5 Drawing Sheets

Related U.S. Application Data continuation-in-part of application No. 13/528,311, filed on Jun. 20, 2012, now abandoned.

(60) Provisional application No. 61/500,781, filed on Jun. 24, 2011.

(51) Int. Cl.
    *A61F 6/00*     (2006.01)
    *A61F 13/20*     (2006.01)
    *A61F 13/15*     (2006.01)

(52) U.S. Cl.
    CPC .... *A61F 13/15772* (2013.01); *A61F 13/2082* (2013.01); *A61F 13/2097* (2013.01); *A61F 13/26* (2013.01); *B29C 69/02* (2013.01); *Y10T 428/1397* (2015.01)

(58) Field of Classification Search
    USPC ......................................................... 246/446
    See application file for complete search history.

(56) References Cited

U.S. PATENT DOCUMENTS

| | | | |
|---|---|---|---|
| 3,131,435 A * | 5/1964 | Cloots | A61F 13/2085 28/119 |
| 3,428,044 A | 2/1969 | Whitehead et al. | |
| 3,460,668 A | 8/1969 | Gerrans | |
| 3,624,746 A | 11/1971 | Grad et al. | |
| 5,078,258 A | 1/1992 | van der Schoot | |
| 5,489,404 A | 2/1996 | LeGrand et al. | |
| 5,788,910 A | 8/1998 | McNelis et al. | |
| 5,931,803 A | 8/1999 | Jackson | |
| 6,221,497 B1 | 4/2001 | Roman et al. | |
| 6,306,238 B1 | 10/2001 | Torniainen et al. | |
| 6,432,075 B1 | 8/2002 | Wada et al. | |
| 6,723,034 B2 | 4/2004 | Durrance et al. | |
| 7,014,637 B1 * | 3/2006 | Denti | A61F 13/2051 206/529 |
| 7,226,436 B2 | 6/2007 | Gorham et al. | |
| 7,704,242 B2 | 4/2010 | LeMay et al. | |
| 8,075,512 B2 | 12/2011 | Sargent, Jr. et al. | |
| 8,616,149 B2 | 12/2013 | Hosokawa et al. | |
| 2004/0199101 A1 | 10/2004 | Lemay et al. | |
| 2005/0197617 A1 | 9/2005 | Gorham et al. | |
| 2008/0255496 A1 | 10/2008 | Sargent et al. | |
| 2009/0057937 A1 | 3/2009 | Takeda | |
| 2009/0321992 A1 * | 12/2009 | Song | A61F 13/2082 264/310 |
| 2011/0106035 A1 * | 5/2011 | Arora | A61F 13/42 604/367 |
| 2011/0209317 A1 * | 9/2011 | Seki | A61F 13/2097 28/118 |
| 2012/0330215 A1 | 12/2012 | Nellenbach et al. | |
| 2013/0019566 A1 | 1/2013 | Schach | |
| 2013/0263862 A1 | 10/2013 | Nellenbach et al. | |

FOREIGN PATENT DOCUMENTS

| | | |
|---|---|---|
| EP | 0230583 A2 | 8/1987 |
| EP | 0332477 | 9/1989 |
| EP | 2428347 A2 | 3/2012 |
| FR | 2696660 B1 | 12/1994 |
| JP | H0465217 A | 3/1992 |
| JP | H05132043 A | 5/1993 |
| JP | 4501269 B2 | 7/2010 |
| WO | 2009018893 A1 | 2/2009 |
| WO | WO2011025022 A1 | 3/2011 |

OTHER PUBLICATIONS

All Office Actions for U.S. Appl. No. 13/910,551 dated Jun. 5, 2013.
All Office Actions for U.S. Appl. No. 13/528,311 dated Jun. 20, 2012.
Whelan, Tony. Polymer Technology Dictionary, Springer Science & Business Media: 1994, pp. 245.
International Search Report and Written Opinion; Application Ser. No. PCT/US2012/043329; dated Jan. 2, 2014, 17 pages.
SPE/ANTEC 1997 Proceedings. Society of Plastics Engineers. CRC Press, Apr. 1997. p. 3195. See attached.

* cited by examiner

METHOD FOR MOVING ARTICLES AND CONTROLLING THE POSITION OF SAME

FIELD OF THE INVENTION

The present invention is generally directed to methods and apparatuses for moving and controlling manufactured articles. Optional treatments and/or inspection of the articles while or after they are moved are also provided by the present invention.

BACKGROUND OF THE INVENTION

There are numerous systems known for moving articles during their manufacture and/or packaging. Some systems employ conveyors or similar apparatuses that randomly transport articles from one location to another, but do not control the orientation or position of the articles so that additional manufacturing steps or inspection can occur in a quality manner. Other systems employ components, such as a cassette, that can maintain orientation of an article as it is moved from one location to another, but the article is typically held statically as it is moved wherein less than the entire article is exposed or otherwise available for additional manufacturing or inspection. What is needed is a method and apparatus that can move an article from one location to another and controllable reorient the article as it is being moved to facilitate treatments or inspection, for example, on multiple portions of the article.

BRIEF DESCRIPTION OF THE DRAWINGS

The following detailed description of specific embodiments of the present invention can be best understood when read in conjunction with the drawings enclosed herewith.

DETAILED DESCRIPTION OF THE INVENTION

Detailed Description

Figure 1:
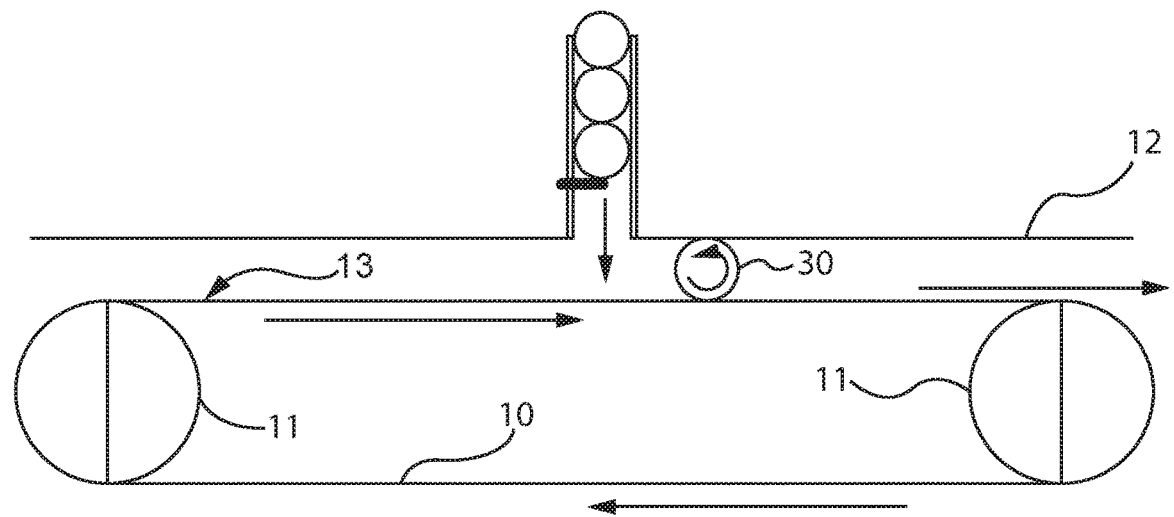
FIG. 1 is a side view of a first embodiment for moving and controlling articles comprising a conveyor and an opposing plate.

The following text sets forth a broad description of numerous different embodiments of the present invention. The description is to be construed as exemplary only and does not describe every possible embodiment since describing every possible embodiment would be impractical, if not impossible. And it will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

It should also be understood that, unless a term is expressly defined in this specification using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). No term is intended to be essential to the present invention unless so stated. To the extent that any term recited in the claims at the end of this patent is referred to in this patent in a manner consistent with a single meaning, that is done for sake of clarity only so as to not confuse the reader, and it is not intended that such a claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

Embodiments described herein generally relate to methods and apparatuses for moving and controlling the position of articles. Additional operations can optionally be performed on the articles due to this control. For example, the articles can be packaged, inspected or treated while and/or after it is moved in a controlled manner. Articles are often inspected for quality purposes. Treatments can include, for example, decorating the article, chemically modifying the article, and exposing it to electromagnetic radiation.

As used herein, the term "article" can include both complete manufactured products and manufactured components that are combined with other components prior to their use or sale to customers.

As used herein, the term "mask" means a component that has the ability to either alter (e.g., limit) or substantially block the transmission of energy therethrough. The masks can have an "open area" which permits some energy transmission. The "open area" may be devoid of all material or may be a material having properties that permits energy transmission from one side of the material to the other.

The figures and detailed description are focused on tampon applicators. The invention however is not limited to tampon applicators unless specifically recited in the claim in question. A representative, non-limiting list of other articles includes toothbrushes, toothbrush handles, packaging, handles for disposable or durable consumer goods, Tampon applicators are generally cylindrical in shape, and therefore are capable of rotation in accordance with the described methods. However, the present invention is not limited to articles that are cylindrical in shape. Some articles may not be cylindrical and yet capable of rotation. And other articles may employ a substantially cylindrical-shaped sleeve or other holding component that is moved so that the article can be rotated and translated according to the methods and apparatuses herein.

Referring now to the figures, FIG. 1 shows a first embodiment that includes an endless conveyor 10, conveyor drive sprockets 11, and an opposing plate 12 that resides over a portion of the conveyor. Conveyor 10 has a planar outer surface 13 for receiving articles. A substantially cylindrically-shaped article, a tampon applicator 30, is disposed between and in contact with conveyor 10 and plate 12. Applicator 30 is both rotated and translated as conveyor 10 is moved due to the frictional forces generated between applicator 30 and the contacted members. The rotation amount substantially matches the translation amount as the tampon applicator travels between the conveyor and plate. Opposing support members, such as plate 12, can be stationary while conveyor 10 is moving or can also move in a similar or different mode.

Figure 2A:
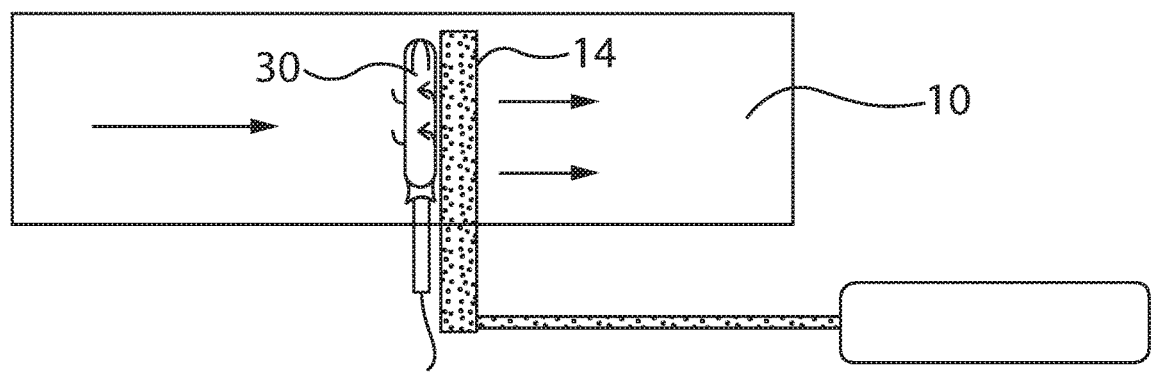
FIGS. 2A-2E depict optional features (e.g., a guide bar or idler roller) that can be employed to manage skewing of an article as the article is rotated and translated.
Figure 2B:
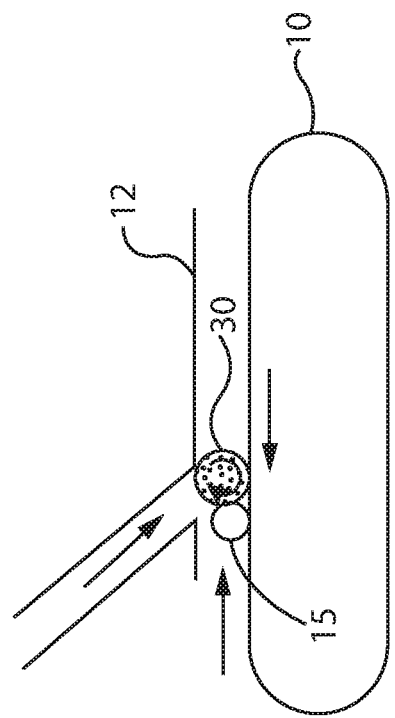
Figure 2C:
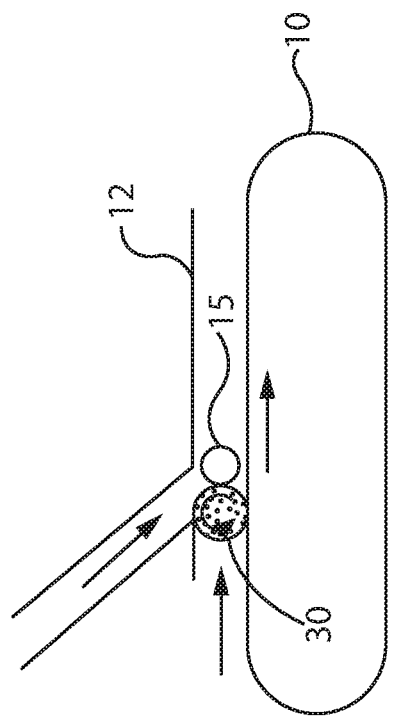
Figure 2D:
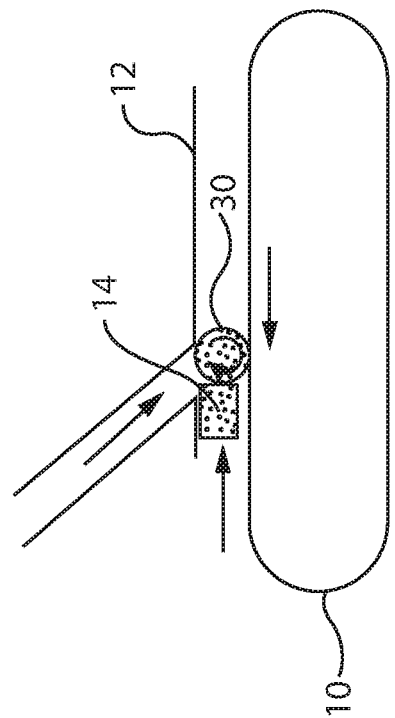
Figure 2E:
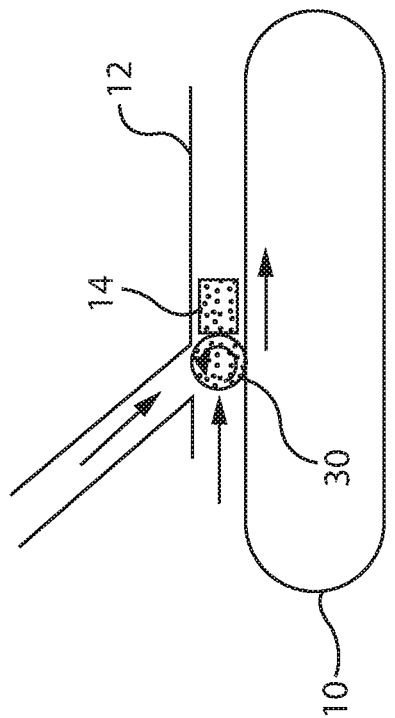
Figure 3:
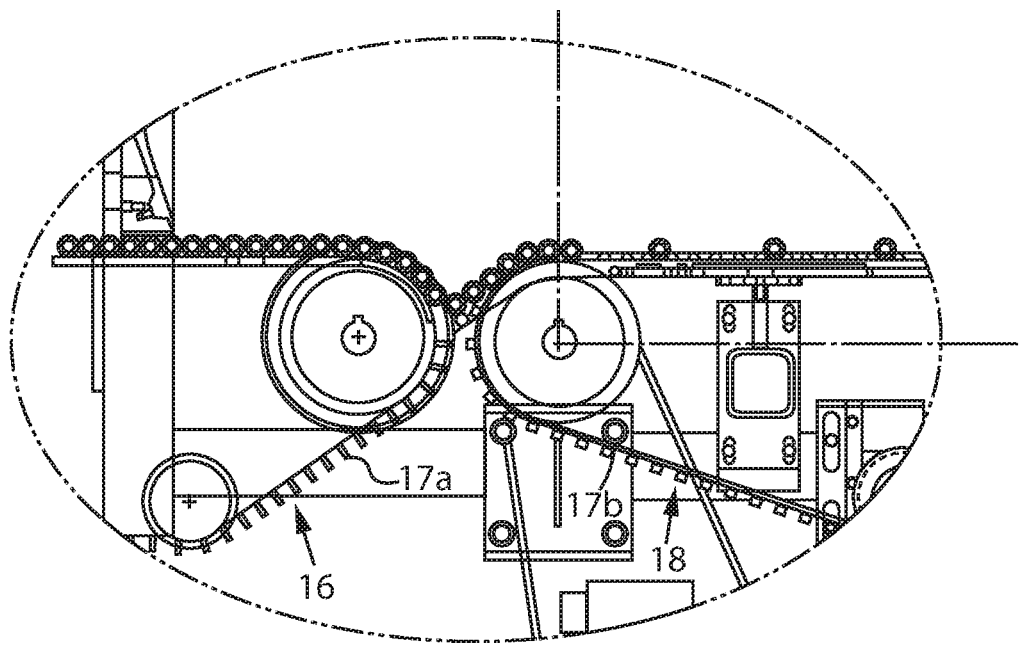
FIG. 3 shows exemplary flighted conveyors that can be used as an alternative to the substantially flat conveyor shown in FIG. 1.
Figure 4:
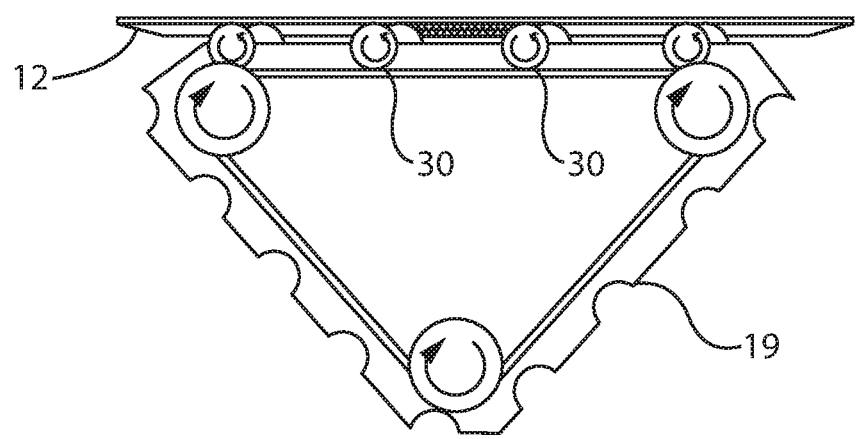
FIG. 4 shows an exemplary pocket conveyor that can be used as an alternative to the substantially flat conveyor shown in FIG. 1.

Some manufactured articles, including some tampon applicators, can have a lengthwise taper or other non-uniformity that can result in the article "walking" left or right as it is rotated according to the embodiment depicted in FIG. 1, rather than translating in a direction that is parallel with the direction of the moving conveyor. A guide bar 14, as shown in FIG. 2A, or similar structure can optionally be employed with articles having non-uniform geometries to maintain a constant translation path (i.e., to control or eliminate article skewing) as the article rotates. FIGS. 2B through 2E depict other embodiments where a guide bar 14 or idler roller 15 is employed to manage skewing of an article. In an alternative embodiment, a flighted conveyor is used instead of flat conveyor 10. FIG. 3 shows two exemplary flighted conveyors 16 and 18 carrying applicators 30. Individual flights, 17a and 17b, on the flighted conveyors can act to control the translation direction of the article and to manage skewing. The flights are preferably lower in height than the article so that the flights do not contact opposing plate 12 when conveyor 10 is operational. Other apparatuses can be employed to move articles while controlling skewing. FIG. 4 depicts a pocket conveyor 19, applicators 30 and a plate 12.

Figure 5:
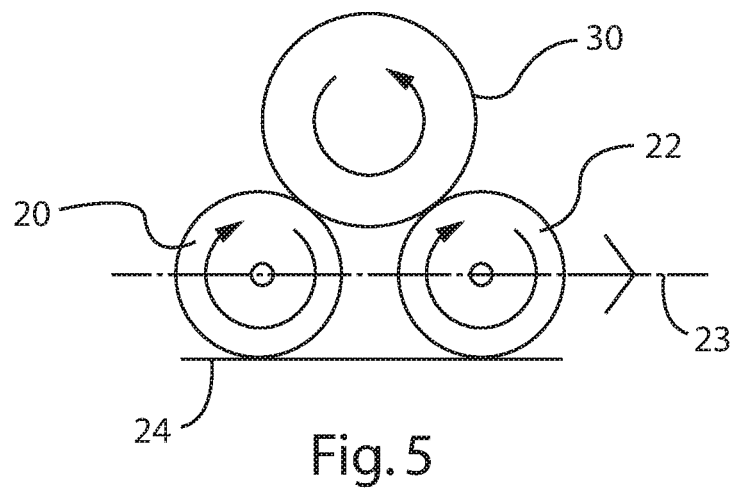
FIG. 5 is another embodiment of the present invention that comprises a first roller and second roller. The first and second rollers rotate upon contact with another member, which in turn causes an article residing between the rollers to rotate.

FIG. 5 depicts another exemplary embodiment, including a first roller 20 and a spaced apart second roller 22. A tampon applicator 30 is placed between first roller 20 and second roller 22. Applicator 30 rotates via frictional forces in response to the rollers being rotated. Rollers 20 and 22 can be associated with an endless roller conveyor (e.g., rollers connected via a chain) that is moved to provide translation of applicator 30 from a first position to a second position in addition to its rotation. To rotate the rollers of a roller conveyor, the rollers can be brought into contact with a stationary member 24 along at least a portion of the roller conveyor path as the roller conveyor is in operation. Arrows are shown to illustrate movement direction of the features shown in FIG. 5. Thus, roller conveyor 23 is operating in a left-to-right direction, with the rollers rotating in a clockwise direction, and applicator 30 rotating in a counter clockwise direction while being translated in a left-to-right direction. It should be appreciated that the directional aspects shown in FIG. 5 are exemplary in nature only, and that alternatives are within the spirit of the present invention.

Rollers, such as those shown in FIG. 5, can also be employed with one or more drums or cylinders. In an exemplary configuration, pairs of rollers are disposed around at least a portion of the circumference of a drum. Both the drum and rollers are rotated simultaneously to expose the tampon applicator (or other article) outer surface to a treatment plate. The treatment plate can be substantially planar or curved. The curvature can be a single direction; for example, to accommodate drum curvature. The plate can also be curved in a second direction to accommodate taper of the tampon applicator.

Inserting mandrels into the tampon applicator (or other hollow article) is another way of controlling the rotation and translation of the applicator in relationship with a treatment plate. The mandrels can be rotated to expose more of the circumferential surface of the applicator. And the mandrels can be translated via a conveyor, drum, or the like.

Figure 6A:
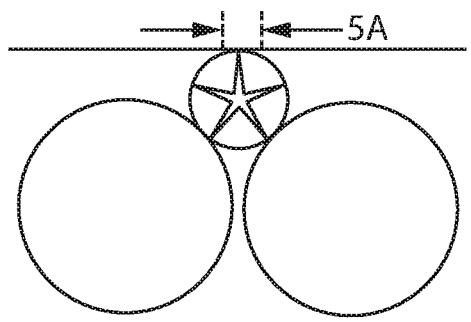
FIGS. 6A and 6B illustrate embodiments that include application of a normal force to an article being rotated and translated.
Figure 6B:
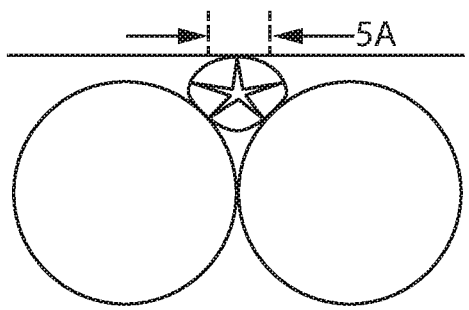

Methods of the present invention can optionally include the step of inspecting or treating an article while the article is moved. The portion of an article that is visible or otherwise available for inspection or treatment while it is moved according to methods herein can vary due to the geometry and size of the article. And many inspection and treatment methods utilize a substantially perpendicular approach. A normal force may optionally be applied to the article that can, depending on the properties of the article, elastically deform the article so that the surface area of the article portion that is positioned perpendicular to the inspection/treatment equipment is increased. Pneumatics or physical structures, for example, can be used to apply a desired normal force. Other devices and means can also be employed to apply the normal force. By way of example only and with reference to the features depicted in FIG. 5, a plate or similar structural member can be positioned opposite the rollers so that applicator 30 is elastically deformed. FIG. 6A depicts the results of a relatively small applied normal force, while FIG. 6B shows an effect of a relatively greater applied normal force. Notice that the surface area SA that would be positioned perpendicular to overlying inspection/treatment equipment is increased with a greater applied normal force.

Activating an activatable colorant within or on an article is one exemplary treatment provided by the present invention. Activatable colorants can include chemicals, monomers and polymers that are capable of being affected by an external stimulus (e.g., an energy source). Examples include thermochromic materials that can change color by a change of temperature, photoreactive materials that can change color through exposure to electromagnetic radiation, and piezochromic materials that can change color via pressure. The color change associated with the activatable colorants can be irreversible, reversible, or quasi-reversible. Activatable colorants can either be coated onto articles or components thereof, such as on films or fibers, or can form an integral part of an article by being added, for example, to the raw materials from which they are made. Exemplary activatable colorants are described in greater detail below.

a) Thermochromic Materials

Thermochromic pigments are organic compounds that effectuate a reversible or irreversible color change when a specific temperature threshold is crossed. A thermochromic pigment may comprise three main components: (i) an electron donating coloring organic compound, (ii) an electron accepting compound and (iii) a solvent reaction medium determining the temperature for the coloring reaction to occur. One example of a commercially available, reversible thermochromic pigment is ChromaZone® Thermobatch Concentrates available from Thermographic Measurements Co. Ltd. Thermochromic pigments and the mechanism bringing about the temperature triggered color change are well-known in the art and are for example described in U.S. Pat. Nos. 4,826,550 and 5,197,958. Other examples of thermochromic pigments are described in U.S. Patent Application Publication No. 2008/0234644A1. Alternatively, the thermosensitive pigment may be of a microcapsule type which is known in the art of thermosensitive pigments.

b) Piezochromic Materials

Any piezochromic materials disclosed in the art are suitable herein as long as they meet the necessary health and safety requirements. An example is disclosed in U.S. Pat. No. 6,330,730. In one example the piezochromic material is thermochromic and responds to a temperature increase caused by applied pressure. In another example the piezochromic material comprises a dye, which is encapsulated into microcapsules. Upon application of pressure these capsules break and release the dye, which then becomes visible. The color intensity is directly linked to the amount of pressure applied. Typical piezochromic materials require a pressure of from 14 to 140 kPa. Most typical piezochromic color change materials can change their color in an irreversible fashion after exertion of pressure. This is due to the fact that the color change was achieved by the destruction of microcapsules, in which the substances for achieving the color change were encapsulated.

c) Photoreactive Materials

Photoreactive materials can change color in response to exposure to electromagnetic radiation. The color change can be irreversible providing a permanent change in color or it can be reversible providing a temporary change in color.

Photochromic materials are those that reversibly change color when exposed to light or changes in light intensity. Photochromic materials typically provide a reversible color change transitioning from a colorless state to a color state upon exposure to light and back to a colorless state when reversed. Exemplary photochromic materials are described in U.S. Pat. Nos. 6,306,409; 6,080,415; and 5,730,961.

Polychromic materials are those which are capable of generating multiple colors. Compounds based upon diacetylene, X—C≡C—C≡C—Y, when polymerized, are known to take on different color properties. Polymerization is typically achieved by exposure to certain types of radiation, such as ultraviolet radiation. Varying the intensity of the radiation causes differing degrees of polymerization, and different colors or shades of colors. Exemplary polychromic materials are disclosed in PCT publication nos. WO 2009/093028A2 and WO 2009/081385 A2. The disclosed compounds can undergo a color change upon irradiation, and have the general structure: X—C≡C—C≡C—Y—(CO)n-QZ wherein X is H, alkyl or —Y—(CO)n-QW; each Y is the same or a different divalent alkylene group; Q is O, S or NR; R is H or alkyl; W is H, alkyl or Z; each Z is the same or a different unsaturated alkyl group; and each n is 0 or 1. The type of radiation that performs the color change reaction with the diacetylene compounds includes laser or non-coherent, broadband or monochromatic radiation. Specific radiation types include ultraviolet, near, mid or far infrared, visible, microwave, gamma ray, x-ray or electron beam.

Another example of a photoreactive material is a thermoplastic material comprising polymer mixed with a charge transfer agent and a photo acid generating agent such as those described in U.S. Patent Application Publication No. 2009/0191476A1. Exposure of the thermoplastic material comprising the charge transfer agent and photo acid generating agent to irradiation can bring about a color change reaction which can be used to create text, artwork, devices or other images and effects. Another application describing photoreactive materials providing permanent color change includes PCT publication no. WO 2009/081385, which describes thermoplastic material comprising polychromic substance wherein the polychromic substance is a functionalized diacetylene having a formula which has a general structure that is described therein.

Activation of photoreactive materials can be achieved using an ultraviolet lamp. One example is the Coil Clean (CC) Series ultraviolet fixtures available from American Ultraviolet (Lebanon, Ind.). Another UVC exposure unit suitable for use in activation of photoreactive materials consists of a metal enclosure containing 8 UV amalgam lamps and 8 ballasts with individual circuits for individual lamp controls and a fan for cooling lamps to maintain temperature. The lamps are 357 mm in length and are available from American Ultraviolet as part number GML750A. Other examples of equipment that may be used for activation of photoreactive materials include the J3825 MonoCure Lamphead from Nordson UV Limited (Berkshire UK) and the 270S UV Lamp Assembly and Power Supply by Integrated Technology. The type of lamp within the unit may be changed to vary the spectral output as needed. Exemplary bulb types include "H", "V", "D" and "Q".

As noted above, one way of associating activatable colorants with an article is by including the colorant with the base material used to manufacture the article. For example, an activatable colorant can be blended with a thermoplastic material that is extruded to form an article. The formed article can then be exposed to a stimulus (e.g., electromagnetic radiation) to activate the colorant, resulting in a visual change in color or shade of at least one portion of the article. The exposure can be manipulated to create a discernable pattern in the article. One way of manipulating the exposure is by manipulating the stimulus or energy source. Another way of manipulating the exposure is through use of masking techniques. A mask with an open area design can be placed between a stimulus and the article. The mask can permit a transmission of the stimulus energy through open areas while preventing or limiting transmission of stimulus energy through masked areas. Multiple masks with similar or different open areas or different energy transmission limitations can be employed, either simultaneously or serially to create various patterns and visual effects.

Figure 7:
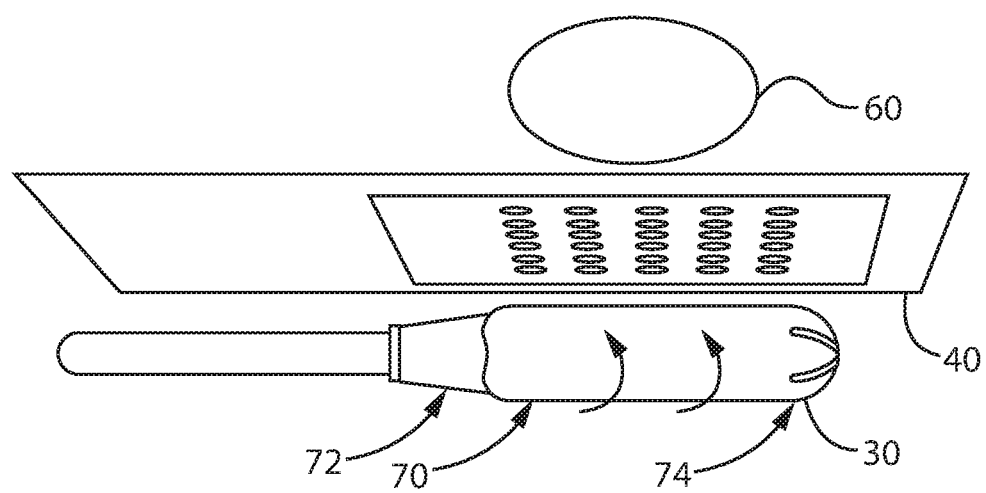
FIG. 7 shows an optional treatment step according to the present invention, wherein the treatment comprises activating colorant associated with an article as the article is rotated and translated.

Masks or patterned plates can be made from a number of different materials and through numerous known techniques. A representative, non-limiting list includes printed nylon films, stenciled aluminum sheets/plates, silk screened quartz, and stenciled stainless steel sheets/plates. Stenciling materials can be done, for example, by photochemical etching or electric discharge machining (EDM). An exemplary mask 40 is shown in FIG. 7. Mask 40 can be placed between an article 30 and an energy source 60 (e.g., a UV lamp) while the article is rotated and translated according to the methods of the present invention. Masks or patterned plates can be stationary while the articles are moved, or they can also move in a similar or different way. In one embodiment, the masks or patterned plates can be created in a belt or continuous structure that can be moved continuously to manage heat and/or other considerations arising from the energy source.

Figure 8:
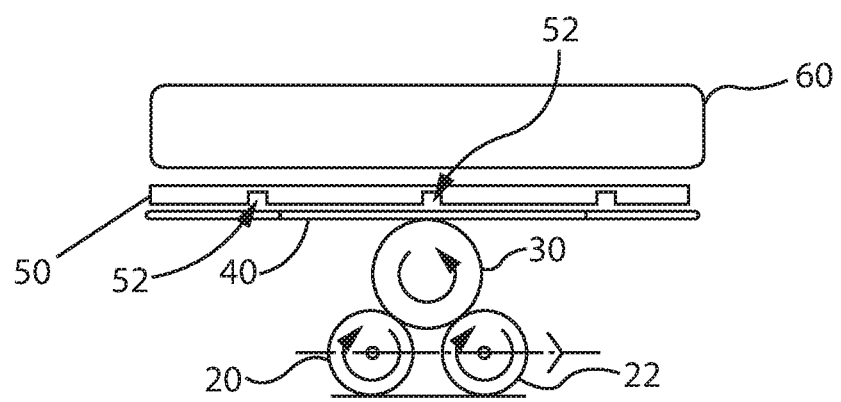
FIG. 8 depicts a similar treatment step as that shown in FIG. 7, along with a shutter device.

Pattern resolution and/or uniformity imparted on or within an article can vary due to a number of factors. One factor is the width of the field of exposure associated with a particular energy source. Some energy sources, e.g., a laser, suitable for activating colorants described herein have a relatively narrow field of exposure. Other energy sources, e.g., a UV lamp, can have a wider field of exposure that inherently contains an energy transmission gradient across its field of exposure. Another factor that can affect the resolution and/or uniformity of an imparted pattern is the positioning of the article or portions thereof with respect to the energy source and mask. For example, at any given time as an article is moved according to methods of the present invention, a first portion of the article may be substantially perpendicular to the mask and energy source while a second portion of the article is positioned at an angle off perpendicular to the mask and energy source. The first portion in this scenario will receive a relatively greater amount of energy than the second portion, which could affect the appearance of the imparted pattern. To improve the resolution or uniformity of a pattern, shutter devices can optionally be employed in conjunction with masks to control or otherwise direct energy transmission in a specified manner. An exemplary embodiment is shown in FIG. 8, wherein an aperture shutter conveyor 50 is employed between mask 40 and energy source 60. Aperture shutter conveyor 50 contains a plurality of individual apertures 52 that are selected to have a width dimension that relates to the dimension of the article portion that is substantially perpendicular to the mask and energy source. Aperture shutter conveyor 50 is preferably operated at a speed that substantially matches the translation velocity of the article as the article is passed under mask 40 and energy source 60.

Treatments other than activating activatable colorants can form a part of the methods of the present invention. For example, articles can be decorated by adding materials (e.g., labels, ink) to the article during and/or after the article is moved. Articles can also be modified to change one or more properties of the articles. For example, the articles can be chemically modified. Chemical modification can include altering the surface energy of the article to make the surface more or less hydrophilic or hydrophobic. For example, the article can be processed with ozone, plasma, or corona treatments to render the surface hydrophilic or more hydrophilic. Chemical modification may also involve grafting hydrophilic/hydrophobic polymers to the article surface. For example, U.S. Pat. Nos. 5,700,559; 5,807,636; and 5,837,377 disclose hydrophilic polymers and methods for grafting the same onto a substrate.

Mechanical and/or heat treatments can also be part of the methods of the present invention. The mechanical/heat treatments can impart texture, textured designs, embossing, sheen differential (shiny or matte) or the like. Methods of the present invention move and control articles so that mechanical/heat treatments can be applied to targeted areas and/or on non-planar surfaces. For example, applicators such as tampon applicators can be textured or patterned via a heated plate or the like after the applicators are molded to simplify the initial mold design or improve molding properties of a starting article. Molded articles can be manufactured to have a visible pattern imparted on portions of its exterior surface via different mold surface properties—e.g., via mold surface polishing. Mold surface polishing or other treatments can be very expensive and can have limited life. The present invention provides for an improvement to the same through a subsequent heat and/or mechanical treatment of the molded article after the article has been blow molded or injection molded. This allows a single mold to be designed and used to manufacture a plurality of articles that can then have different surface appearances through different post-molded mechanical/heat treatments. In an alternative embodiment of the present invention, a combination of mold surface manipulation and post-mold treatment can be used to create a finished article.

The subsequent heat and/or mechanical treatment comprises exposing portions of the article to heat and/or physical contact. When heat alone is employed to impart a visible pattern, the heat exposure is preferably above the melting point of the thermoplastic material (e.g., polyethylene, polypropylene, or mixtures thereof) from which the article is made. It is believed that this exposure at least partially remelts the exposed portions. The remelting or second heat history creates a visible pattern and/or sheen difference in the article. A combination of heat and physical manipulation may be employed also. The heat exposure in such a combination may be near or above the softening point or melting point of the thermoplastic material, or may alternatively be below the softening point of the material. And the physical manipulation can take a variety of forms including, but not limited to pressure and mechanical abrasion. Lastly, a mechanical treatment without added heat may also be used impart a desired pattern on the article's exterior surface. Portions of the surface may be abraded to render a smoother or rougher surface relative to the non-treated areas of the surface to yield a desired visible and/or tactile pattern.

The heat exposure is preferably conducted by physically contacting the article with a heated component, such as a heated plate alluded to above. Components other than a patterned plate may however be employed to create the pattern. For example, a patterned and heated sleeve (that is a single component or defined by multiple components that are brought together to encapsulate the article) can be used to at least partially remelt exterior portions of the article. Contacting the article with a heated component may result in only remelting exterior portions without also embossing or indenting the same portions, such that the remelted portions are substantially coplanar with portions adjacent the remelted portions. Alternatively, contacting may both remelt and emboss/indent exterior portions of the article to provide a visual and tactile pattern. In one embodiment, articles are rotated and translated against a stationary heated component to define a pattern. In another exemplary embodiment, a heat source (e.g., an iron or laser) can moved in relation with a moving or static article to provide a pattern on several portions of the article.

The heat and/or mechanical treatments on a post-molded article can create designs or textures that extend minimally above or below a surface of the article. This can allow for imparting design aspects on articles such as toothbrushes and feminine care applicators that come into contact with human tissue without being significantly uncomfortable. By way of example only, the heat and/or mechanical treatment may result in a surface design, pattern, texture, or the like that extends above or below the surface by 1-50 microns, 1-10 microns, or 1-5 microns. For thin-walled articles, such as, for example, feminine care applicators, the extension can be less than about 25%, 10%, or 5% of the wall thickness.

A variety of treatments have been discussed above. One skilled in the art should appreciate that combinations of treatments are also contemplated by the present invention. By way of example only, a molded article comprising activatable colorant can incur multiple post-molded treatments. All or a selected region of the article can first be exposed to a stimulus to activate the colorant. The article can then be exposed to a heat and/or mechanical treatment that can alter the initial color change and/or impart an additional visible pattern or design. The visible appearance changes from the color activation and the separate heat/mechanical treatment can be distinct from one another or complementary to one another. Other treatment combinations are also possible.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for altering the appearance of molded articles, the method comprising the steps of:
    a. providing a plurality of articles that have been extrusion, blow or injection molded, each of the plurality of articles having an exterior surface section having a cylindrical shape, the cylindrical shape having a longitudinal axis;
    b. feeding a first article of the plurality of articles to a conveyor;
    c. transporting the first article along a transporting direction to a treatment station, wherein the longitudinal axis of the first article is oriented transversely to the transporting direction at the treatment station;
    d. activating an activatable colorant of the first article by exposing the first article to at least one energy source at the treatment station, thereby causing a color change in the first article;
    e. manipulating the exposure of the first article to the energy source by rotating the first article about the longitudinal axis thereof while simultaneously transporting the first article along the transporting direction, proximate to a plurality of masks in succession disposed between the first article and the energy source, to create a first discernable pattern in the first article; wherein each of the masks has an open area, and wherein each of the masks has a different open area;
    f. feeding a second article of the plurality of articles to the conveyor;
    g. transporting the second article along the transporting direction to the treatment station, wherein the longitudinal axis of the second article is oriented transversely to the transporting direction at the treatment station;
    h. activating an activatable colorant of the second article by exposing the second article to the at least one energy source at the treatment station, thereby causing a color change in the second article; and
    i. manipulating the exposure of the second article to the energy source by rotating the second article about the longitudinal axis thereof while simultaneously transporting the second article along the transporting direction, proximate to the plurality of masks, to create a second discernable pattern in the second article.

2. The method of claim 1, wherein each of the articles has a lengthwise taper.

3. The method of claim 2, further comprising a step of guiding the articles to reduce walking.

4. The method of claim 1, wherein the conveyor is flighted.

5. The method of claim 1, wherein the steps of activating an activatable colorant each further comprise a step of providing electromagnetic energy to the articles.

6. The method of claim 1, wherein each of the first article and second article comprises a thermoplastic material, and wherein the activatable colorant of the first article and the second article is mixed with the thermoplastic material.

7. The method of claim 1, further comprising a step of heating the first article to impart a visible pattern and/or create a sheen difference between one portion of the first article compared to another portion of the first article.

8. The method of claim 1, wherein each of the plurality of articles is a tampon applicator.

* * * * *